(12) United States Patent
Isaac

(10) Patent No.: US 7,771,486 B2
(45) Date of Patent: Aug. 10, 2010

(54) CUP ASSEMBLY OF AN ORTHOPAEDIC JOINT PROSTHESIS

(75) Inventor: Graham Isaac, Huddersfield (GB)

(73) Assignee: Depuy International, Ltd., Leeds (GB)

( * ) Notice: Subject to any disclaimer, the term of this patent is extended or adjusted under 35 U.S.C. 154(b) by 49 days.

(21) Appl. No.: 11/071,496

(22) Filed: Mar. 3, 2005

(65) Prior Publication Data

US 2006/0015186 A1 Jan. 19, 2006

(51) Int. Cl.
*A61F 2/30* (2006.01)
(52) U.S. Cl. .................................................. 623/23.43
(58) Field of Classification Search ............. 623/23.43, 623/22.21, 22.23, 22.27, 22.31, 22.32, 22.33, 623/22.38, 22.39
See application file for complete search history.

(56) References Cited

U.S. PATENT DOCUMENTS

| | | | | |
|---|---|---|---|---|
| 3,918,102 | A * | 11/1975 | Eichler | 623/22.39 |
| 4,883,490 | A * | 11/1989 | Oh | 623/22.39 |
| 5,405,402 | A | 4/1995 | Dye et al. | |
| 5,625,577 | A | 4/1997 | Kunii | |
| 5,702,478 | A * | 12/1997 | Tornier | 623/22.24 |
| 5,755,807 | A | 5/1998 | Anstaett et al. | |
| 6,310,619 | B1 | 10/2001 | Rice | |
| 6,310,627 | B1 | 10/2001 | Sakaguchi | |
| 6,404,426 | B1 | 6/2002 | Weaver | |
| 6,908,486 | B2 * | 6/2005 | Lewallen | 623/22.21 |
| 2001/0026272 | A1 | 10/2001 | Feld | |
| 2004/0236455 | A1 | 11/2004 | Woltman | |
| 2004/0236456 | A1 | 11/2004 | Pieper | |
| 2004/0236457 | A1 | 11/2004 | Stabelfeldt | |
| 2005/0021148 | A1 * | 1/2005 | Gibbs | 623/22.12 |

FOREIGN PATENT DOCUMENTS

| | | |
|---|---|---|
| DE | 19926816 | 2/2001 |
| EP | 0 120 595 A1 | 10/1984 |
| EP | 0 577 179 A1 | 1/1994 |
| EP | 0 927 545 A2 | 7/1999 |
| EP | 1 221 674 A2 | 7/2002 |
| FR | 2707479 | 1/1995 |
| GB | 2 216 015 A | 10/1989 |
| WO | WO 00/59581 A1 | 10/2000 |
| WO | WO 01/01235 A1 | 1/2001 |
| WO | WO 01/35342 A1 | 5/2001 |
| WO | WO 01/64106 A1 | 9/2001 |
| WO | WO 02/29758 A2 | 4/2002 |

OTHER PUBLICATIONS

EP, Search Report, GB0220514.4.
David Baraff, Partitioned Dynamics, The Robotics Institute, Mar. 1997.

(Continued)

*Primary Examiner*—Alvin J Stewart

(57) ABSTRACT

A cup assembly of an orthopaedic joint prosthesis comprises a cup-shaped component which is rotationally symmetrical about a polar axis, and which is hollow to receive a rotationally symmetrical head of a component of the joint prosthesis. The cup-shaped component has a groove in its outer surface which extends around the component in a plane which is approximately perpendicular to the polar axis. A spacer component comprises a plurality of spaced apart spacer elements which are connected by a spacer web. The spacer web, but not the spacer elements, can be fitted into the groove in the outer surface of the cup-shaped component.

23 Claims, 3 Drawing Sheets

OTHER PUBLICATIONS

Figure 1:
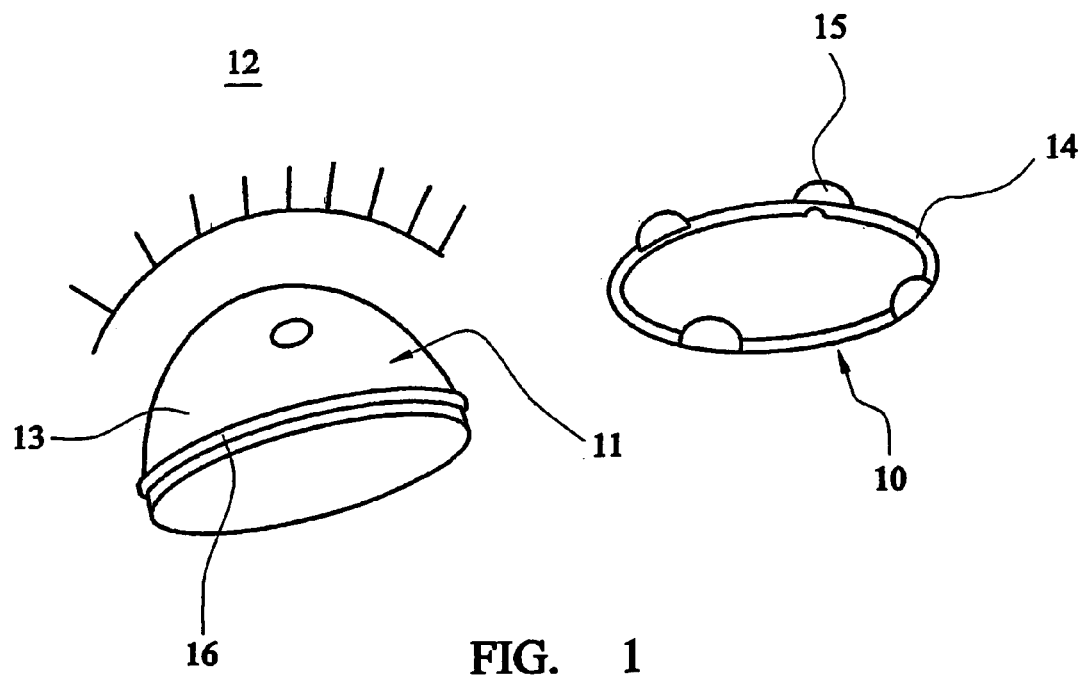

Fred S. Azar, A Deformable Finite Element Model of the Breast for Predicting Mechanical Deformations under External Perturbations, 2001.

C.W.J.Oomens, Deformation Analysis of a Supported Buttock Contact, BED-vol. 50, 2001.

Pascal Vollino, Versatile and Efficient Techniques for Simulating Cloth and Other Deformable Objects, Miralab 1998.

David E. Breen, Predicting the Drape of Woven Cloth Using Interacting Particles, ECRC-94-16.

Fabio Ganovelli, Indroducing Multiresolution Representation in Deformable Object Modeling.

Donald H. House, Towards Simulating Cloth Dynamics Using Interacting Particles, ECRC Feb. 7, 1996.

David E. Breen, A Particle-Based Model for Simulating the Draping Behavior of Woven Cloth, ECRC-94-19.

* cited by examiner

CUP ASSEMBLY OF AN ORTHOPAEDIC JOINT PROSTHESIS

This invention relates to a cup assembly of an orthopaedic joint prosthesis.

The replacement of joints such as hip and shoulder joints commonly involves use of prostheses which include a cup component. The cup component is hollow so that it can receive the head of a stem component. The cup component can be affixed using bone cement by which a bond is formed between the patient's bone tissue and the facing surface of the cup component.

It can be desirable to control the space between a cup component and the facing surface of the patient's bone so that the layer of bone cement in that space is continuous and so that the surface of the cup component does not contact the bone tissue.

It is known to position spacer components between the surface of a cup component and the facing surface of bone tissue. For example, discrete spacer elements, or a spacer ring, can be fixed to a cup component prior to implantation.

The present invention provides a cup assembly of an orthopaedic joint prosthesis in which a spacer component comprising spacer elements, interconnected by a spacer web, is located on a cup-shaped component with the spacer web in a groove which extends perpendicular to the polar axis of the cup-shaped component.

Accordingly, in one aspect, the invention provides a cup assembly of an orthopaedic joint prosthesis which comprises:
- a cup-shaped component which is rotationally symmetrical about a polar axis, and which is hollow to receive a rotationally symmetrical head of an component of the joint prosthesis, the cup-shaped component having a groove in its outer surface which extends around the component in a plane which is approximately perpendicular to the polar axis, and
- a spacer component which comprises a plurality of spaced apart spacer elements which are connected by a spacer web, in which the spacer web, but not the spacer elements, can be fitted into the groove in the outer surface of the cup-shaped component.

The invention provides a spacer arrangement for fitting to or on an acetabular cup in artificial hip joint replacement surgery, said cup being intended to be placed adjacent to a prepared bone surface with the spacer arrangement thereby defining a space between the bone surface and a facing surface of the cup so as to receive a cement filling of said space, in which the spacer arrangement is made of implantable material and comprises a spacer string which can be fitted on or to said facing surface of the cup and which has a set of spacer elements arranged along the length of the string.

The cup assembly of the present invention has the advantage that the spacer elements can provide control over the spacing between the external surface of the cup component and the surface of the bone tissue. With suitable preparation of the bone for receiving the cup component, this can ensure that there is a mantle of cement over the cup component surface whose thickness is approximately uniform.

Providing the spacer elements as a spacer component, connected by a spacer web, has the advantage that the location of the spacer elements relative to one another is controlled.

The spacer component of the invention has the advantage of minimising the resistance to flow of bone cement in the space between the cup-shaped component and the bone tissue. This arises because the spacer web is located in a groove in the surface of the cup-shaped component. It is known to provide grooves in the external surface of a cup-shaped component of a joint prosthesis, for example to receive X-ray visible marker wires, or to aid in cement keying. Such grooves can have a width of at least about 0.5 mm, preferably at least about 0.75 mm. The width is generally not more than about 1.5 mm, for example not more than about 1.0 mm. The depth of such grooves is often at least about 0.5 mm, preferably at least about 0.75 mm. The depth is generally not more than about 1.5 mm, for example not more than about 1.0 mm.

Preferably, the spacer web fits wholly within the groove in the cup component so that it provides little or no resistance to flow of bone cement. However, the web need not fit wholly within the groove, and the benefits of the present invention can be obtained when the web protrudes from the groove. The spacer web can approximately fill the groove so that it is a secure fit in the groove. The spacer web can be a recessed fit in the groove. The groove is then able to assist in keying the component to the surrounding mantle of bone cement.

The cup-shaped component is rotationally symmetrical about the polar axis. Preferably, the component is approximately spherical. However, other shapes are contemplated, for example in which the radius of curvature of the component varies from the pole towards the equator.

The external surface of the cup-shaped component can extend through an angle of arc as much as 180 degrees, although smaller components, for example with an angle of arc of up to 175 degrees, or up to 170 degrees, will be suitable for many applications.

Preferably, the angle subtended at the centre of the cup-shaped component by the perimeter of the groove is not more than about 120 degrees, preferably not more than about 105 degrees, more preferably not more than about 90 degrees. The angle is measured at the centre of the component on the equator.

Preferably, the ratio of the diameter of the groove in which the spacer web fits (measured on the external surface of the cup component) to the external diameter of the spherical surface cup component at the equator (which might require extrapolation of the surface if the surface does not extend through an angle of arc as much as 180 degrees) is not more than about 0.8, more preferably not more than about 0.7, for example not more than about 0.6.

Preferably, the spacer web is generally circular so that it is configured to fit into the groove in the cup-shaped component, and the material of the spacer web is sufficiently rigid to be self-supporting in that configuration.

Preferably, the spacer web and the spacer elements are formed of the same material. For example the web and the elements can be formed as a single component by moulding.

Preferably, the material of the spacer web or the material of the spacer elements or both is resorbable after the assembly is implanted.

Preferably, the material of the spacer web or the material of the spacer elements or both is the same as the material of a bone cement. In another aspect, the invention provides a kit which comprises the assembly of the invention and a bone cement material.

Preferably, the outwardly facing surface of the spacer elements is generally rounded, for example approximately part-spherical, or approximately hemispherical. This has the advantage of minimising the resistance to flow of bone cement around the elements to form a uniform mantle of bone cement.

Preferably, the spacer elements have a transverse dimension (which will be the diameter when they are circular when viewed from above) of not more than about 5 mm, more preferably not more than about 3 mm.

Preferably, the spacer component includes at least three spacer elements. Preferably, the spacer elements are spaced apart approximately uniformly along the spacer web.

The spacer component can readily be fitted to the surface of the cup component, either immediately prior to implantation of the cup component, or the spacer component may be fitted on to the cup component as part of the manufacturing process.

Preferably, the spacer web is broken at one point to enable it to be opened resiliently to be fitted into the groove in the cup-shaped component. Preferably, the diameter of the groove is greater at the external surface of the cup component than at the base of the groove so that the spacer web can relax resiliently as it is fitted into the groove. This can help to retain the spacer component on the cup component.

The spacer component can be arranged to follow any required arcuate path on the surface of the cup component, and may be pre-formed to take up the required path, or may be sufficiently flexible, or deformable, so as to be able to be manipulated to take up the required path when fitted to the surface of the cup component.

In a preferred form, the spacer component takes the form of a continuous, or near continuous, ring, and the successive spacer elements may be angularly spaced apart at approximately equal angles from each other with reference to the axis of the assembly.

In one embodiment of the invention, the ring is made of uniform cross-section, (preferably circular) and part-spherical, or hemi-spherical pips may be arranged with arcuate spacing therebetween along the length of the ring (or part ring) to form the spacer elements.

In a practical embodiment, the ring may be a thin polymethylmethacrylate (PMMA) ring which is capable of fitting into a groove in the surface of the cup component. The spacer elements may be also made of PMMA.

The cup component of the assembly can comprise a polymeric material, for example a polyolefin, especially ultrahigh molecular weight polyethylene. The cup component of the invention might be metallic, for example a stainless steel, or a titanium alloy.

Figure 2:
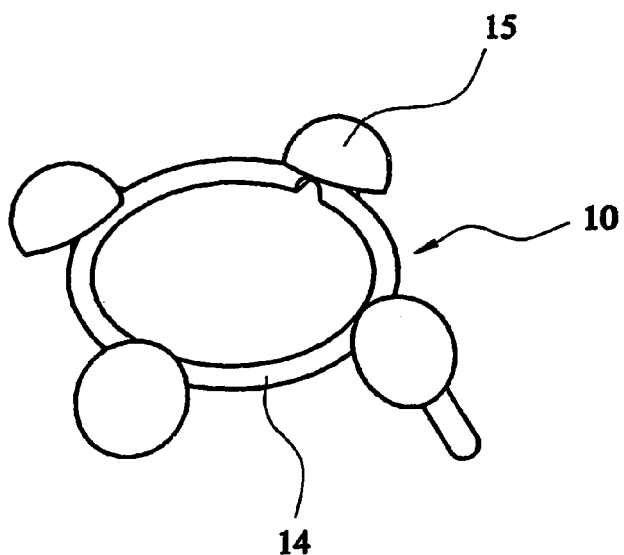
Figure 3:
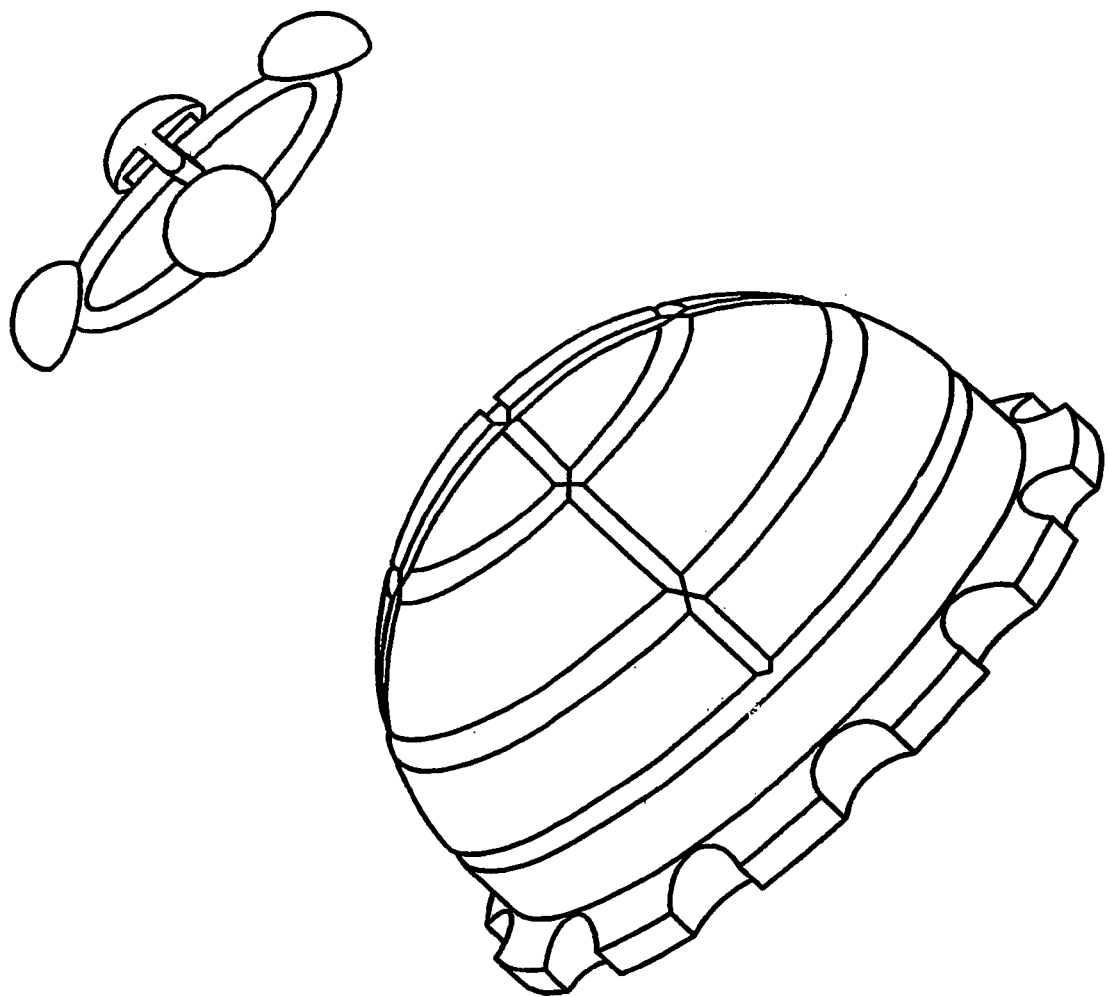

Embodiments of cup assemblies according to the invention will now be described, by way of example only, with reference to the accompanying drawings, in which:

FIG. 1 is an exploded diagrammatic illustration of a prepared bone surface and an acetabular cup with grooves into which a spacer arrangement according to the invention can be fitted; p FIG. 2 is a perspective and part plan view illustration of a spacer arrangement according to the invention in more detail; and FIG. 3 is an exploded view showing in more detail the shape and construction of a practical embodiment of acetabular cup and spacer arrangement.

Figure 4:
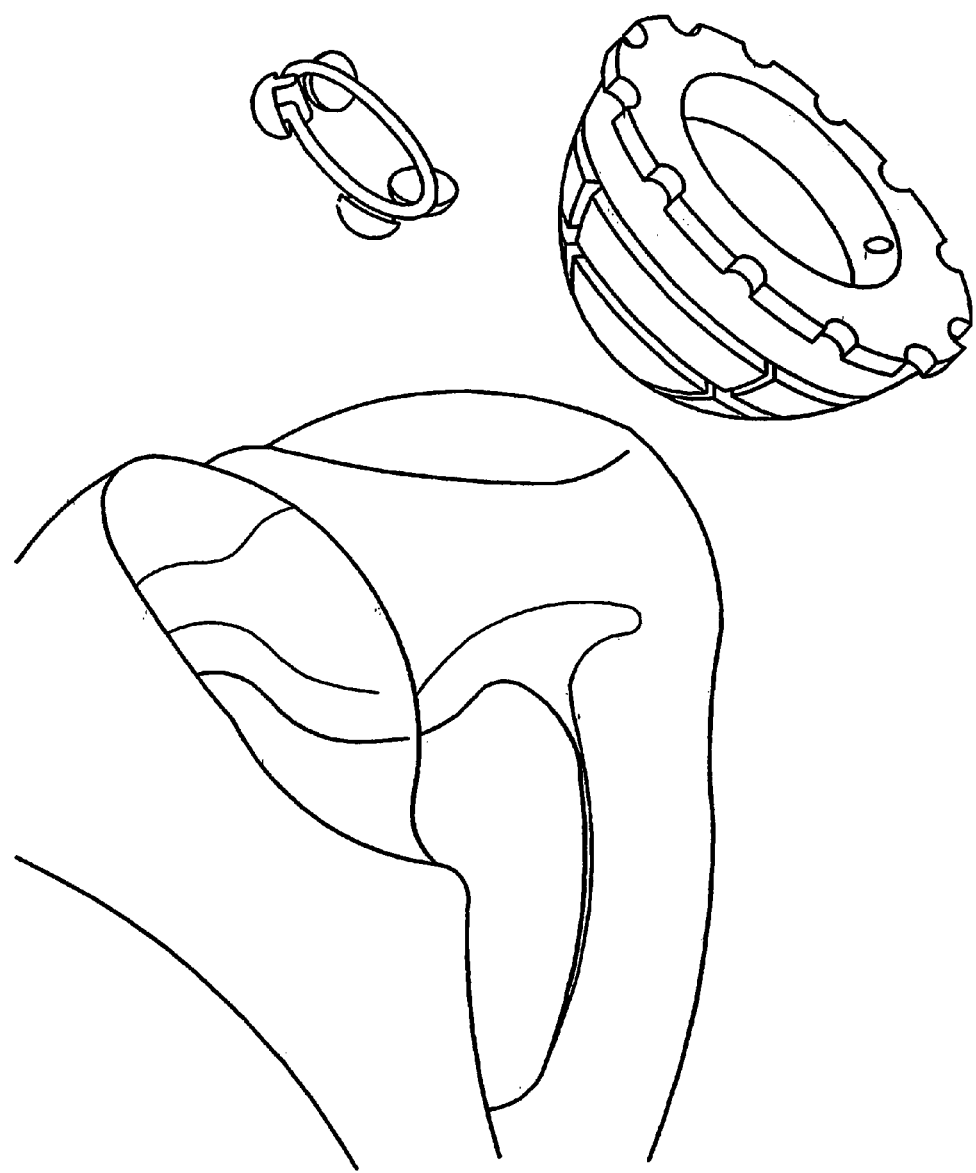

FIG. 4 is an exploded, perspective view of a spacer arrangement in accordance to one embodiment of the invention arranged near an acetabulum.

Referring now to the drawings, a cup assembly according to the invention is designated generally by reference 10. It comprises an acetabular cup component 11 for use in artificial hip joint replacement surgery. The cup component 11 is intended to be placed adjacent to a prepared bone surface 12 with the spacer component 10 (when fitted to the cup 11) defining a space between the bone surface and the approximately spherical surface 13 of the cup 11 so as to receive a cement mantle within the space.

The spacer component 10 is made of implantable material, and comprises a spacer web which in the illustrated embodiment is a thin ring 14, and which has a set of spacer elements 15 arranged along its length.

The spacer component can be readily fitted to or on the surface of the cup component 11, either immediately prior to placement of the cup component 11, or the spacer component may be installed on the cup component as part of the manufacturing process.

The spacer web can be arranged to follow any required arcuate path on the surface of the cup component 11, and may be pre-formed to take up the required path, or may be sufficiently flexible, or deformable, so as to be capable of being manipulated to take up the required path when fitted to the surface of the cup component.

In the preferred form, as illustrated in FIG. 2, the spacer web takes the form of a continuous, or near continuous, ring, and the successive spacer elements 15 are angularly spaced apart from each other at approximately equal angles with respect to the axis of the assembly.

The web is made of uniform cross-section, preferably circular, and part-spherical or hemispherical pips may be arranged with arcuate spacing between them, to form the spacer elements 15.

In a practical embodiment, the spacer web may be a thin PMMA ring which is capable of fitting into the groove on the surface of the cup component. The spacer elements may also be made of PMMA, and be attached as "pods" to the web, either by being formed integrally with it (for example, by moulding) or by being formed separately and then bonded to the web.

The groove in the surface of the cup 11 into which the ring may fit may be arranged generally parallel to the cup equator, just as with the grooves 16 in the component shown in the drawings. The size of the spacer web is such that it fits into a groove in the external surface of the component which subtends an angle at the centre of the cup component of about 40 degrees.

The preferred embodiment of the invention, as illustrated in the drawings, provides a solution to the problems encountered with known spacer arrangements, by providing a thin PMMA ring which will fit into the grooves of current acetabular ranges. To this ring are attached PMMA pods to make a continuous structure, and which can be clipped onto the cup and act as a spacer. The spacer ring is compatible with current products, and may be packed separately, or in the same packaging as the acetabular cup. It is envisaged that the ring will be clipped on during the procedure, which gives the surgeon the choice of whether to use the ring, or not. It also does not restrict the method of terminal sterilisation. It would also be possible to carry out trial reductions prior to cementation.

The invention claimed is:

1. A cup assembly of an orthopaedic joint prosthesis, comprising:
    a cup-shaped component that is rotationally symmetrical about a polar axis, is hollow to receive a rotationally symmetrical head of a component of the joint prosthesis, and has an outer surface, and a groove in the outer surface that extends around the cup-shaped component in a plane that is approximately perpendicular to the polar axis; and
    a spacer component comprising a plurality of spaced apart spacer elements that are connected by a generally planar spacer web, wherein a portion of the spacer web is configured to fit into the groove, and wherein the spacer web is broken.

2. The cup assembly of claim 1, wherein the spacer web is generally circular.

3. The cup assembly of claim 1, wherein the spacer web and the spacer elements are formed of the same material.

4. The cup assembly of claim 1, wherein the material of one of the spacer web and spacer elements is resorbable.

5. The cup assembly of claim 1, wherein the outwardly facing surface of the spacer elements is part-spherical.

6. The cup assembly of claim 1, wherein an angle subtended at the center of the equator of the cup-shaped component by the groove is not more than about 120 degrees.

7. The cup assembly of claim 1, wherein the plurality of spaced apart spacer elements includes at least three spacer elements spaced apart along the spacer web.

8. The cup assembly of claim 7, wherein the spacer elements are approximately equally spaced apart along the spacer web.

9. The cup assembly of claim 1, wherein the spacer web is configured to be sufficiently rigid to be self-supporting when a portion of the spacer web is in disposed in the groove.

10. The cup assembly of claim 1, wherein the spacer component is a ring.

11. The cup assembly of claim 1, wherein an angle subtended at the center of the equator of the cup-shaped component by the perimeter of the groove is not more than about 120 degrees.

12. The cup assembly of claim 1, wherein the diameter of the groove is greater at the external surface of the cup component than at the base of the groove.

13. The cup assembly of claim 1, wherein the cup component has an equatorial diameter, located at the equator of the cup-shaped component, and a groove in the outer surface that extends around the cup-shaped component in a plane that is substantially perpendicular to the polar axis and located on a minor diameter, the minor diameter being less than the equatorial diameter.

14. The cup assembly of claim 1, wherein the ratio of the minor diameter to the equatorial diameter is not more than 0.8.

15. A cup assembly of an orthopaedic joint prosthesis which comprises:
   a cup-shaped component that is rotationally symmetrical about a polar axis, is hollow to receive a rotationally symmetrical head of a component of the joint prosthesis, and has an outer surface and a groove in the outer surface that extends around the component in a plane which is approximately perpendicular to the polar axis; and
   a generally planar spacer component comprising a plurality of spaced-apart spacer elements that are connected by a spacer web, wherein a portion of the spacer web is configured to be disposed within the groove, and wherein the spacer web broken at one point to enable the spacer web to be opened resiliently to be fitted into the groove.

16. The cup assembly of claim 15, wherein the spacer web is generally circular.

17. The cup assembly of claim 15, wherein the material of one of the spacer web and spacer elements is resorbable.

18. The cup assembly of claim 15, wherein the outwardly facing surface of the spacer elements is part-spherical.

19. The cup assembly of claim 15, wherein an angle subtended at the center of the equator of the cup-shaped component by the perimeter of the groove is not more than about 120 degrees.

20. The cup assembly of claim 15, wherein the plurality of spaced apart spacer elements includes at least three spacer elements spaced apart along the spacer web.

21. The cup assembly of claim 20, wherein the spacer elements are approximately equally spaced apart along the spacer web.

22. The cup assembly of claim 15, wherein the spacer web is configured to be sufficiently rigid to be self-supporting when a portion of the spacer web is in disposed in the groove.

23. A cup assembly of an orthopaedic joint prosthesis which comprises:
   a cup-shaped component which is rotationally symmetrical about a polar axis, and which is hollow to receive a rotationally symmetrical head of an component of the joint prosthesis, the cup-shaped component having a groove in its outer surface which extends around the component in a plane which is approximately perpendicular to the polar axis; and
   a spacer component comprising a plurality of spaced-apart spacer elements, each of which is connected by a generally planar spacer web, wherein a portion of the spacer web is configured to be disposed within the groove in the outer surface of the cup-shaped component, and wherein a spacer web connecting two spaced-apart spacer elements is broken to enable the spacer component to be opened to permit the portion of the spacer web to be disposed within the groove of the cup-shaped component.

* * * * *